US011499138B2

(12) United States Patent
Nishiyama et al.

(10) Patent No.: US 11,499,138 B2
(45) Date of Patent: Nov. 15, 2022

(54) METHOD FOR MANUFACTURING PERIPHERAL NERVE CELLS

(71) Applicants: NATIONAL UNIVERSITY CORPORATION GUNMA UNIVERSITY, Maebashi (JP); KABUSHIKI KAISHA YAKULT HONSHA, Minato-ku (JP)

(72) Inventors: Masahiko Nishiyama, Maebashi (JP); Susumu Rokudai, Maebashi (JP); Shinji Yoshiyama, Maebashi (JP); Hiroyuki Takahashi, Minato-ku (JP)

(73) Assignees: NATIONAL UNIVERSITY CORPORATION GUNMA UNIVERSITY, Maebashi (JP); KABUSHIKI KAISHA YAKULT HONSHA, Minato-ku (JP)

( * ) Notice: Subject to any disclaimer, the term of this patent is extended or adjusted under 35 U.S.C. 154(b) by 0 days.

(21) Appl. No.: 16/335,889

(22) PCT Filed: Oct. 20, 2017

(86) PCT No.: PCT/JP2017/037922
§ 371 (c)(1),
(2) Date: Mar. 22, 2019

(87) PCT Pub. No.: WO2018/074567
PCT Pub. Date: Apr. 26, 2018

(65) Prior Publication Data
US 2020/0017829 A1 Jan. 16, 2020

(30) Foreign Application Priority Data

Oct. 21, 2016 (JP) .............................. JP2016-207211

(51) Int. Cl.
C12N 5/00 (2006.01)
C12N 5/0797 (2010.01)
C12N 5/074 (2010.01)
C12N 5/0735 (2010.01)
C12N 5/0793 (2010.01)
C12N 5/079 (2010.01)

(52) U.S. Cl.
CPC ......... C12N 5/0623 (2013.01); C12N 5/0606 (2013.01); C12N 5/0618 (2013.01); C12N 5/0619 (2013.01); C12N 5/0696 (2013.01); C12N 2506/00 (2013.01); C12N 2506/45 (2013.01)

(58) Field of Classification Search
CPC .. C12N 5/0623; C12N 5/0619; C12N 5/0618; C12N 2506/00; C12N 5/0606; C12N 5/0696
USPC ....................................................... 435/325
See application file for complete search history.

(56) References Cited

U.S. PATENT DOCUMENTS 9,133,435 B2 9/2015 Takahashi et al.
2013/0011921 A1 1/2013 Hishida et al.
2013/0149287 A1 1/2013 Livesey et al.
2013/0183674 A1 7/2013 Studer et al.
2016/0257930 A1 9/2016 Kemp

FOREIGN PATENT DOCUMENTS

JP    2013-532961 A    8/2013
TW    201114896 A1    5/2011
WO    WO 2011/149762 A2    12/2011
WO    WO 2012/115120    8/2012
WO    WO 2015/055987    4/2015

OTHER PUBLICATIONS

Pomp (Stem Cells, 2005, vol. 23, p. 923-930).*
Nakamura (Cytotechnology, 2016, vol. 68, p. 409-417).*
Peripherin definition, WikiPedia, 2020.*
Nadal-Nicolas, Inv. Opthal. & Visual Sci., 2009, vol. 50, No. 8, p. 3860-3868.*
Kreitzer (Am J Stem Cell, 2013, vol. 2, No. 2, p. 119-131).*
Written Opinion Translation for PCT/JP2017/037922.*
Guo (Journal of Investigative Dermatology, (May 2016) vol. 136, No. 5, Suppl. 1, pp. S132).*
Extended European Search Report dated Mar. 24, 2020, in Patent Application No. 17861471.5, 10 pages.
Schwartz, M. P. et al., "Human pluripotent stem cell-derived neural constructs for predicting neural toxicity", Proceedings of the National Academy of Sciences, XP055259334, vol. 112, No. 40, Sep. 21, 2015, pp. 12516-12521.
International Search Report dated Jan. 23, 2018 in PCT/JP2017/037922 filed on Oct. 20, 2017.
Lee, K. S. et al., "Human Sensory Neurons Derived from Induced Pluripotent Stem Cells Support Varicella-Zoster Virus Infection," Plos One, Dec. 2012, vol. 7, Issue 12, e53010, pp. 1-10.
Pomp, O. et al., "Generation of Peripheral Sensory and Sympathetic Neurons and Neural Crest Cells from Human Embryonic Stem Cells," Stem Cells, 2005, vol. 23, pp. 923-930.
Nakamura, M. et al., "Differentiation patterns of mouse embryonic stem cells and induced pluripotent stem cells into neurons," Cytotechnology, 2016, vol. 68, pp. 409-417.

(Continued)

Primary Examiner — Michael C Wilson
(74) Attorney, Agent, or Firm — Oblon, McClelland, Maier & Neustadt, L.L.P.

(57) ABSTRACT

Provided is a method for efficiently manufacturing high-purity peripheral nerve cells from undifferentiated cells. The method for manufacturing peripheral nerve cells from undifferentiated cells having an ability to differentiate into peripheral nerve cells includes the following steps (a) and (b): (a) culturing undifferentiated cells having an ability to differentiate into peripheral nerve cells to induce differentiation into neural progenitor cells without detaching a grown colony from a culture vessel; and (b) detaching the neural progenitor cells produced in the step (a) from the culture vessel, then seeding the cells at a seeding density of $2 \times 10^5$ to $6 \times 10^5$ cells/cm$^2$ to a culture vessel, and culturing the cells for 14 to 42 days.

7 Claims, 3 Drawing Sheets

(56) References Cited

OTHER PUBLICATIONS

Shi, F. et al., "BMP4 induction of sensory neurons from human embryonic stem cells and reinnervation of sensory epithelium," European Journal of Neuroscience, 2007, vol. 26, pp. 3016-3023.
Guo, X. et al., "Derivation of sensory neurons and neural crest stem cells from human neural progenitor hNP1," Biomaterials, 2013, vol. 34, pp. 4418-4427.
Gunther, K. et al., "Rapid Monolayer Neural Induction of induced Pluripotent Stem Cells Yields Stably Proliferating Neural Stem Cells," Journal of Stem Cell Research and Therapy, Jun. 2016, vol. 6, Issue 6, pp. 1-6.
Nat, R., "From Human Pluripotent Stem Cells to Peripheral Neurons," INTECH, Pluripotent Stem Cells—From the Bench to the Clinic, Chapter 15, 2016, pp. 307-329.
Combined Taiwanese Office Action and Search Report dated Nov. 2, 2021 in Taiwanese Patent Application No. 106136079 (with English translation), 17 pages.
Catalog, Neural Stem Cells, R&D Systems, Bio-techne BR_NSC_16595 Accessed at (link below) Apr. 4, 2022 (8 pages). https://resources.rndsystems.com/images/site/rnd-systems-nsc-br2.pdf.
Chambers et al, "Highly efficient neural conversion of human ES and iPS cells by dual inhibition of SMAD signaling", *Nat Biotechol.* 2009, vol. 27, No. 3 (13 pages).
Chambers et al, "Combined small molecule inhibition accelerates developmental timing and converts human pluripotent stem cells into nociceptors", Biotechnol. 2012, vol. 30, No. 7, pp. 715-720 (17 pages).
Qi et al, "Combined small-molecule inhibition accelerates the derivation of functional, early-born, cortical neurons from human pluripotent stem cells", Nat Biotechnol, 2017, vol. 35, No. 2 (26 pages).
Katoh et al, "FGFR2-related pathogenesis and FGFR2-targeted therapeutics (Review)", *International Journal of Molecular Medicine*, 2009, vol. 23: pp. 307-311.
Zhou et al, "Conversion of Mouse Epiblast Stem Cells to an Earlier Pluripotency State by Small Molecules", Journal of Biological Chemistry, 2010, vol. 285, No. 39, pp. 29676-29680.
Gudernova et al, "Multikinase activity of fibroblast growth factor receptor (FGFR} inhibitors SU5402, PD173074, AZD1480, AZD4547 and BGJ398 compromises the use of small chemicals targeting FGFR catalytic activity for therapy of short-stature syndromes", Human Molecular Genetics, 2016, vol. 25, No. 1, pp. 9-23.

\* cited by examiner

METHOD FOR MANUFACTURING PERIPHERAL NERVE CELLS

TECHNICAL FIELD

The present invention relates to a method for manufacturing peripheral nerve cells.

BACKGROUND ART

Peripheral nerves mean all nerves except for central nerves (the brain and spinal cord), and are including motor nerves and sensory nerves and are responsible for input of information from the outside to the central nerves and output from the central nerves to effector organs such as muscle. Peripheral neuropathy is caused by, for example, diabetes, excessive intake of alcohol, vitamin B deficiency, or side effects of drugs such as anticancer drugs, and causes various symptoms such as atrophy of muscle, occurrence of numbness or pain, lightheadedness, diarrhea, and constipation, and in some cases, such symptoms are irreversible and are not cured.

In recent years, research on regenerative medicine that aims to compensate damaged nerves, tissues, organs, etc. by inducing differentiation of undifferentiated cells (stem cells) is under way. If nerve cells can be obtained from stem cells, i.e., embryonic stem cells (ES cells) or induced pluripotent stem cells (iPS cells), they can be used in various research in vitro and in vivo regarding neuropathy as well as regenerative medicine, and a technique to induce differentiation of stem cells into nerve cells is currently attracting attention.

Conventionally, as a technique for producing peripheral nerve cells by inducing differentiation of iPS cells, a method by growing colonies of iPS cells using mouse embryonic fibroblasts (MEPs) as feeder cells, then detaching the iPS cells, performing adherent culture for differentiation into neural progenitor cells, and subsequently culturing the cells for 14 days for differentiation into peripheral nerve cells has been reported (Non Patent Literature 1).

However, the peripheral nerve cells produced by this method are not as highly pure as they can be used for in vitro or in vivo studies on neuropathy and eventually for regenerative medicine, and the differentiation-inducing rate is also not high, and techniques for efficiently manufacturing high-purity peripheral nerve cells have been required.

CITATION LIST

Non Patent Literature

Non Patent Literature 1: PLOS ONE December 2012 Vol. 7, issue 12, e53010

SUMMARY OF THE INVENTION

Technical Problem

The present invention relates to providing a method for efficiently manufacturing high-purity peripheral nerve cells from undifferentiated cells.

Solution to Problem

The present inventors have studied the conditions for inducing differentiation of undifferentiated cells having the ability to differentiate into peripheral nerve cells and have found that high-purity peripheral nerve cells can be efficiently manufactured by culturing the undifferentiated cells as colonies to induce differentiation into neural progenitor cells and to further induce differentiation into peripheral nerve cells in a confluent state by increasing the cell seeding density.

That is, the present invention relates to the following 1) to 9).

1) A method for manufacturing peripheral nerve cells from undifferentiated cells having an ability to differentiate into peripheral nerve cells, the method comprising the following steps (a) and (b):
  (a) culturing undifferentiated cells having an ability to differentiate into peripheral nerve cells to induce differentiation into neural progenitor cells without detaching a grown colony from a culture vessel; and
  (b) detaching the neural progenitor cells produced in the step (a) from the culture vessel, then seeding the cells at a seeding density of $2 \times 10^5$ to $6 \times 10^5$ cells/cm$^2$ to a culture vessel, and culturing the cells for 14 to 42 days.

2) The method according to 1), wherein the step (a) further comprises the following step (a'):
  (a') culturing the undifferentiated cells having an ability to differentiate into peripheral nerve cells by adherent culture without using feeder cells.

3) The method according to 1) or 2), wherein the undifferentiated cells having an ability to differentiate into peripheral nerve cells are iPS cells.

4) The method according to any one of 1) to 3), wherein a culture period of the culturing in the step (b) is 21 to 28 days.

5) The method according to any one of 1) to 4), wherein a medium for the culturing in the step (b) includes NGF.

6) The method according to any one of 1) to 4), wherein 85% or more of the cells in a culture after the culturing in the step (b) are positive for expression of at least one of βII tubulin, peripherin, and Brn3a.

7) Peripheral nerve cells differentiated from undifferentiated cells having an ability to differentiate into peripheral nerve cells, wherein 85% or more of the cells in a culture of the peripheral nerve cells are positive for expression of at least one of βIII tubulin, peripherin, and Brn3a.

8) Peripheral nerve cells differentiated from undifferentiated cells having an ability to differentiate into peripheral nerve cells, wherein an mRNA level of Brn3a expressed in the peripheral nerve cells is 30 times or more that in the undifferentiated cells.

9) The peripheral nerve cells according to 7) or 8), wherein the undifferentiated cells having an ability to differentiate into peripheral nerve cells are iPS cells.

Effects of the Invention

According to the present invention, high-purity peripheral nerve cells having the same morphology and properties as those of peripheral nerve cells in a living body can be efficiently manufactured from undifferentiated cells having the ability to differentiate into peripheral nerve cells. Since the peripheral nerve cells of the present invention can be manufactured from cells such as induced pluripotent stem cells prepared from a patient's own somatic cells, it is possible to simultaneously solve the problem of shortage of donors and the problem of rejection response in the field of regenerative medicine for peripheral neuropathy.

BRIEF DESCRIPTION OF THE DRAWINGS

FIG. 1 shows fluorescence activated cell sorting (FACS) data of a culture containing peripheral nerve cells (Example 1), where upper graph: βIII tubulin, middle graph: peripherin, lower graph: Brn3a.

FIG. 2 shows FACS data of a culture containing peripheral nerve cells (Comparative Example 1), where upper graph: βIII tubulin, middle graph: peripherin, lower graph: Brn3a.

DESCRIPTION OF EMBODIMENTS

Figure 1:
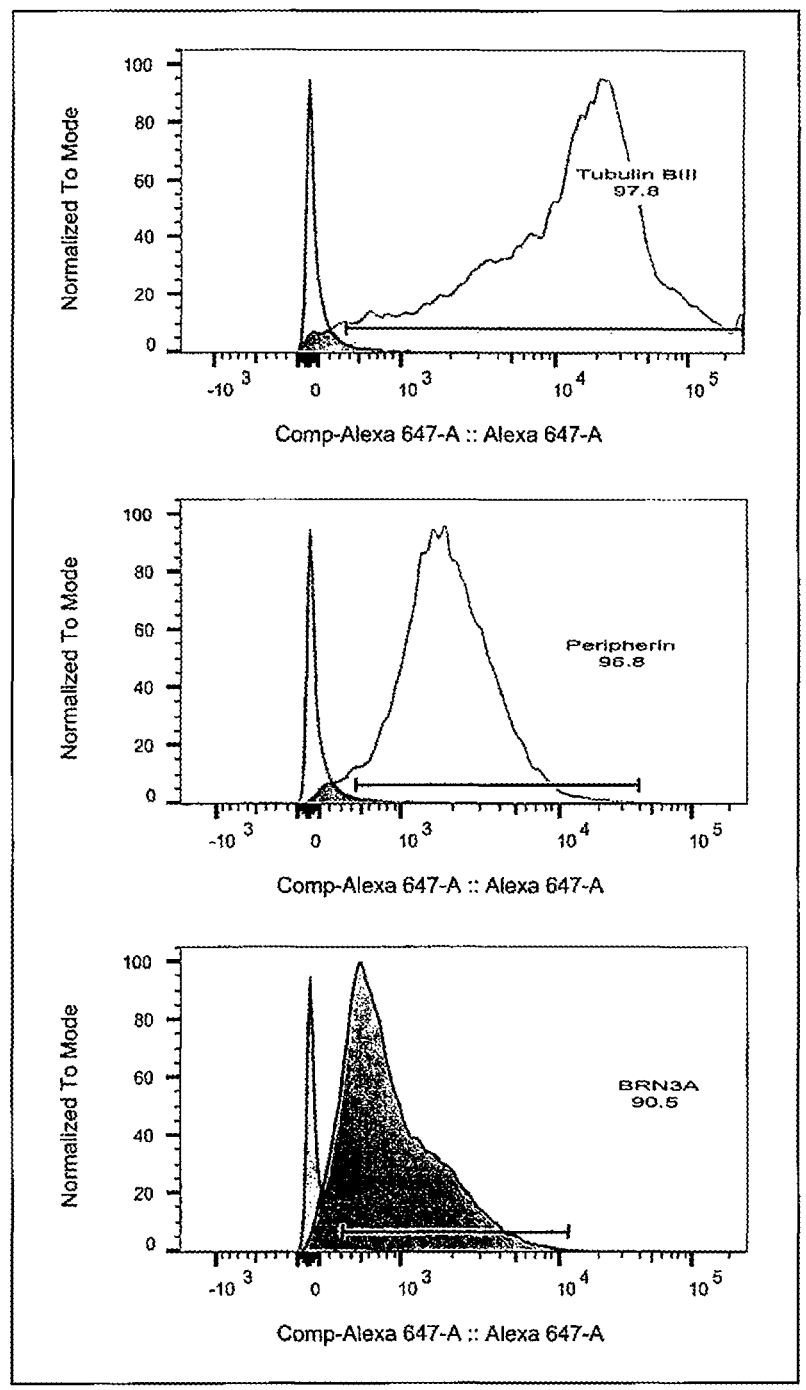

The method for manufacturing peripheral nerve cells of the present invention comprises the following steps (a) and (b):

(a) culturing undifferentiated cells having an ability to differentiate into peripheral nerve cells to induce differentiation into neural progenitor cells without detaching a grown colony from a culture vessel; and (b) detaching the neural progenitor cells produced in the step (a) from the culture vessel, then seeding the cells at a seeding density of $2 \times 10^5$ to $6 \times 10^5$ cells/cm$^2$ to a culture vessel, and culturing the cells for 14 to 42 days.

The "undifferentiated cell having an ability to differentiate into a peripheral nerve cell" (hereinafter, also simply referred to as an "undifferentiated cell") used in the present invention may be any undifferentiated cell having an ability to differentiate into a peripheral nerve cell, and examples thereof include embryonic stem cells (ES cells) and induced pluripotent stem cells (iPS cells). ES cells and iPS cells are preferred from the viewpoint of the supply amount of cells, and iPS cells are more preferred.

Here, the term "iPS cell" refers to a cell reprogrammed (initialized) so as to have pluripotency as in ES cells by introducing a specific factor into a mammalian somatic cell or an undifferentiated stem cell (K. Takahashi and S. Yamanaka (2006) Cell, WO 2007/069666).

As the iPS cells used in the present invention, known induced pluripotent stem cells and all induced pluripotent stem cells equivalent thereto are included as long as they have the above functions, and the cell source, introduction factor, and introduction method are not particularly limited.

Step (a):

This step is a step of culturing undifferentiated cells having the ability to differentiate into peripheral nerve cells to induce differentiation into neural progenitor cells without detaching a colony of the grown (matured) undifferentiated cells from a culture vessel.

In particular, it is preferable to include a step (a') of culturing undifferentiated cells having the ability to differentiate into peripheral nerve cells by adherent culture without using feeder cells.

Here, the term "feeder cell" refers to a cell to be supplementarily used to prepare an environment necessary for proliferation and differentiation of a cell as a target in cell culture. Conventionally, ES cells or iPS cells are co-cultured with feeder cells, such as mouse embryonic fibroblasts, for the purpose of supplementing nutrients (including intercellular adhesion factors) that cannot be supplemented only with the medium and additives, but it is preferable to perform the cell culture in this step without using feeder cells. This step is preferably performed by adherent culture in a culture vessel coated with a material having cell adhesion properties (scaffold material).

As the scaffold material, cell adhesion factors, such as fibronectin (FN), vitronectin (VN), and laminin, are known, and it is particularly preferred to use a basement membrane matrix (growth factor-reduced Matrigel™ (Matrigel™ GFR), manufactured by Corning Incorporated), which is a mixture of cell adhesion factors including laminin.

The medium to be used in the culture of this step may be any medium that is suitable for culturing undifferentiated cells. For example, a medium prepared by appropriately adding an additive to a base medium, such as a ReproFF2 medium and a DMEM/F12 medium, suitable for feeder cell free culture of animal cells, in particular, undifferentiated cells can be used.

Here, examples of the additive include antibiotics, such as penicillin and streptomycin; basic fibroblast growth factor (bFGF); and serum replacements, such as KnockOut™ Serum Replacement.

The cell seeding density at the start of culture is not particularly limited and is, for example, $1 \times 10^3$ to $5 \times 10^4$ cells/cm$^2$, preferably $5 \times 10^3$ to $2 \times 10^4$ cells/cm$^2$, in the culture vessel.

The culture conditions are not particularly limited, and the culture temperature is, for example, 30° C. to 40° C., preferably 36° C. to 38° C., and the $CO_2$ concentration is, for example, 1% to 10%, preferably 4% to 6%. The culture is preferably performed until the density of colonies of undifferentiated cells reaches about 50% in the culture vessel.

The culture vessel is not particularly limited as long as it can culture cells, and examples thereof include dish (60-mm tissue culture dish, manufactured by Corning Incorporated).

Although induction of ES cells or iPS cells is often performed after culture of the cells and detachment of the cells from the culture vessel for removing the feeder cells, in this step, undifferentiated cells can be differentiated, as colonies, into neural progenitor cells when the density of colonies of the undifferentiated cells reaches about 50% without detaching the undifferentiated cells from the culture vessel.

Here, the term "detachment" refers to that cells adhering to a culture vessel are peeled off from the culture vessel using, for example, a cell dissociation solution.

The medium for differentiating into neural progenitor cells can be prepared by using a medium for animal cells, such as a DMEM/F12 medium, as a base medium and appropriately adding to the medium various nutrition sources necessary for maintenance and proliferation of cells and ingredients necessary for differentiation.

Examples of the additive include antibiotics, such as penicillin and streptomycin; serum replacements, such as KSR (Knockout™ Serum Replacement); FGFR inhibitors (e.g., SU5402); γ-secretase inhibitors (e.g., RO4929097); GSK3 inhibitors (e.g., CHIR99021), TGF-β family inhibitors (e.g., A83-01); ALK inhibitors (e.g., LDN-193189); Purmorphamine (PMA); and retinoic acid.

The culture conditions are not particularly limited, and the culture temperature is, for example, 30° C. to 40° C., preferably 36° C. to 38° C., and the $CO_2$ concentration is, for example, 1% to 10%, preferably 4% to 6%. The culture period is preferably 6 to 14 days, more preferably 8 to 12 days.

Step (b):

This step is a step of detaching the neural progenitor cells produced in the step (a) from the culture vessel, then seeding the cells at a seeding density of $2 \times 10^5$ to $6 \times 10^5$ cells/cm$^2$ to a culture vessel, and culturing the cells for 14 to 42 days.

That is, the neural progenitor cells produced in the step (a) are detached from the culture vessel before differentiation into peripheral nerve cells, and differentiation is induced at a seeding density of the cells increased to a confluent state (state where cells adhered to the entire bottom and side surfaces of the culture vessel). Consequently, the differentiation efficiency is increased, and peripheral nerve cells highly expressing a differentiation marker can be produced.

The neural progenitor cells can be detached using a known cell dissociation solution (for example, Accutase™ (Innovative Cell Technologies, Inc.) or Dispase™ (Godo Shusei Co., Ltd.)).

The detached and collected neural progenitor cells are appropriately washed and are then seeded in a culture vessel coated with the same scaffold material as that used in the step (a). The seeding density on this occasion is $2\times10^5$ to $6\times10^5$ cells/cm² in the culture vessel. Such a seeding density enables culturing at a 90% to 100% confluent state.

Specifically, for example, seeding can be performed by changing the culture vessel to one having a culture area of about ½ to 1 time, preferably about ⅔ times, that of the culture vessel (for example, cells obtained from a 60-mm diameter culture dish are transferred to two wells of a 6-well plate (diameter: 35 mm)).

The medium used for the culture preferably contains a nerve growth factor (NGF). Examples of the base medium include media for animal cells, such as a DMEM/F12 medium, as in those used in the step (a), and the medium can be prepared by appropriately adding thereto ingredients necessary for differentiation.

Examples of the additive include, in addition to NGF, antibiotics, such as penicillin and streptomycin; serum replacements, such as KSR (Knockout™ Serum Replacement); N2-supplement; B27-supplement; insulin; neurotrophin-3 (NT-3); brain-derived neurotrophic factor (BDNF); glial cell line-derived growth factor (GDNF); vitamins (ascorbic acid, etc.); dibutyl cAMP; bone morphogenetic protein-4 (BMP-4); and amino acids.

The culture conditions are, for example, preferably 30° C. to 40° C., more preferably 36° C. to 38° C. and a $CO_2$ concentration of, for example, 1% to 10%, preferably 4% to 6%.

The culture period is 14 to 42 days and is more preferably 14 to 35 days, even more preferably 14 to 28 days, and particularly preferably 21 days from the viewpoint of increasing the incidence of expression of a differentiation marker.

The thus-differentiated peripheral nerve cells can be isolated from the culture solution using a known cell dissociation solution (for example, Accutase™ (Innovative Cell Technologies, Inc.) or Dispase™ (Godo Shusei Co., Ltd.)).

The peripheral nerve cells manufactured by the method of the present invention express βIII tubulin, peripherin, and Brn3a, which are known as differentiation markers of peripheral nerve cells, and have the same morphology and properties as those of peripheral nerve cells in in-vivo. In addition, the method of the present invention can manufacture peripheral nerve cells with high purity compared to conventional methods. Here, the purity of the peripheral nerve cells can be evaluated by the expression level of, for example, βIII tubulin, peripherin, or Brn3a. The high purity means, for example, that the expression level of Brn3a is 30 times or more, specifically 30 to 300 times, that of the undifferentiated cells before differentiation.

The method of the present invention can provide peripheral nerve cells in the culture after completion of culturing in the step (b) such that 85% or more of the cells are positive for expression of at least one of βII tubulin, peripherin, and Brn3a, in particular, 85% or more of the cells are positive for expression of all of βIII tubulin, peripherin, and Brn3a. That is, the rate of peripheral nerve cells in the culture prepared by the method of the present invention is 85% or more, and the method of the present invention is significantly excellent in differentiation efficiency into peripheral nerve cells.

The peripheral nerve cells thus-manufactured by the method of the present invention can be used as a cell formulation for regenerative medicine, and the culture containing peripheral nerve cells differentiated from undifferentiated cells by the method of the present invention can be used as a raw material in research, regenerative medicine, or a cell formulation.

Examples of the cell formulation using peripheral nerve cells manufactured by the method of the present invention include cell sheets prepared by networking the peripheral nerve cells and cell fibers.

EXAMPLES

Example 1

(1) Preparation and Culturing of Human iPS Cells (Step (a') in Step (a))

Human iPS cells (JCRB363 cells, hereinafter, referred to as iPS cells) were purchased from JCRB cell bank. One cell cryopreservation tube of the iPS cells (about $1\times10^4$ cells/cm²) were seeded in a 60-mm dish (Corning Incorporated) coated with growth factor-reduced Matrigel™ (Matrigel GFR, Corning Incorporated).

Coating of the dish with Matrigel™ GFR was performed by diluting a Matrigel™ GFR stock solution 50 times with a DMEM/F12 medium (containing 1% L-glutamine, FUJIFILM Wako Pure Chemical Corporation), pouring it to the dish so as to cover the entire surface, and leaving it to stand at room temperature for 3 hours. The dish was stored at 4° C. until use.

The culturing was performed in a ReproFF2 medium (ReproCELL Inc.) containing 1% penicillin-streptomycin (FUJIFILM Wako Pure Chemical Corporation) and 10 ng/mL basic fibroblast growth factor (bFGF, ReproCELL Inc.) under conditions of 5% $CO_2$ and 37° C. The medium was replaced by a new one every two or three days, and subculture was performed when iPS colonies grew.

(2) Differentiation into Neural Progenitor Cells (Step (a))

After the density of the iPS cell colonies reached about 50% in the culture vessel, the iPS cells were washed with a DMEM/F12 medium (containing 1% L-glutamine, FUJIFILM Wako Pure Chemical Corporation) without being detached from the dish, and were cultured in a DMEM/F12 medium containing ingredients shown below under conditions of 5% $CO_2$ and 37° C. for 10 days. The medium was replaced by a new one every two or three days.

Medium additives: 10% KnockOut™ serum replacement (KSR, Thermo Fisher Scientific Inc.), 1% penicillin-streptomycin, 0.3 μM SU5402 (Sigma-Aldrich), 1.0 μM RO4929097 (Cellagen Technology), 5 μM CHIR99021 (BioVision Incorporated), 1 μM A83-01 (Cellagen Technology), 0.2 μM LDN-193189 (Axon Medchem), and 0.1 μM retinoic acid (Sigma-Aldrich).

(3) Differentiation into Peripheral Nerve Cells (Step (b))

The iPS-derived cells differentiated into neural progenitor cells were detached from the dish using Accutase™ (Innovative Cell Technologies, Inc.). The collected iPS-derived cells were separated from the medium by centrifugation (1000 rpm, 5 minutes) and were suspended in a DMEM/F12 medium not containing differentiation factors and so on. Centrifugation (1000 rpm, 5 minutes) was performed again to wash the iPS-derived cells.

The iPS-derived cells obtained as a precipitate were seeded in two wells of a 6-well plate (diameter of each well:

35 mm, Iwaki & Co., Ltd.) coated with Matrigel™ GFR (the area corresponds to ⅔ times the area of the 60-mm dish, cell seeding density: 4×10$^5$ cells/cm$^2$), and were cultured in a DMEM/F12 medium (containing 1% L-glutamine, FUJIFILM Wako Pure Chemical Corporation) containing ingredients shown below under conditions of 5% $CO_2$ and 37° C. for 21 days (culturing in a confluent state). The medium was replaced by a new one every two or three days.

Medium additives: 10% KSR (Thermo Fisher Scientific Inc.), 1% penicillin-streptomycin (FUJIFILM Wako Pure Chemical Corporation), ×1 N2 supplement (Thermo Fisher Scientific Inc.), 10 ng/mL neurotrophin-3 (NT-3, Miltenyi Biotec), 10 ng/mL brain-derived neurotrophic factor (BDNF, Miltenyi Biotec), 10 ng/mL nerve growth factor (NGF, Thermo Fisher Scientific Inc.), 10 ng/mL glial cell line-derived growth factor (GDNF, FUJIFILM Wako Pure Chemical Corporation), 200 μM ascorbic acid (Sigma-Aldrich), and 0.5 mM dibutyryl cAMP (Enzo Life Science International, Inc.).

(4) Isolation of Peripheral Nerve Cells

The medium was removed, and the cells were washed with PBS, then mixed with Acutase™, and left to stand at room temperature for 5 to 15 minutes. The culture vessel was slowly tilted, and after confirmation of detachment of the cells, the peripheral nerve cells were collected with a pipette.

Example 2

Peripheral nerve cells were manufactured as in Example 1 except that the culture period in Example 1 (3) was changed to 42 days.

Comparative Example 1

Peripheral nerve cells were manufactured as in Example 1 except that the seeding of iPS-derived cells differentiated into neural progenitor cells to a culture container in Example 1 (3) was changed to seeding to two 60-mm dishes coated with Matrigel™ GFR (the area was twice that of the 60-mm dish, cell seeding density: 1×10$^5$ cells/cm$^2$) (culturing in a non-confluent state).

Comparative Example 2

Example 1 (3) was changed to the following method.

The iPS-derived cells differentiated into neural progenitor cells were cultured without being detached from the dish in a DMEM/F12 medium (containing 1% L-glutamine, FUJIFILM Wako Pure Chemical Corporation) containing ingredients shown below under conditions of 5% $CO_2$ and 37° C. for 14 days (iPS-derived cells differentiated into neural progenitor cells were, without being detached from the dish, differentiated into peripheral nerve cells). The medium was replaced by a new one every two or three days.

Medium additives: 10% KSR (Thermo Fisher Scientific Inc.), 1% penicillin-streptomycin (FUJIFILM Wako Pure Chemical Corporation), ×1 N2 supplement (Thermo Fisher Scientific Inc.), 10 ng/mL neurotrophin-3 (NT-3, Miltenyi Biotec), 10 ng/mL brain-derived neurotrophic factor (BDNF, Miltenyi Biotec), 10 ng/mL nerve growth factor (NGF, Thermo Fisher Scientific Inc.), 10 ng/mL glial cell line-derived growth factor (GDNF, FUJIFILM Wako Pure Chemical Corporation), 200 μM ascorbic acid (Sigma-Aldrich), and 0.5 mM dibutyryl cAMP (Enzo Life Science International, Inc.).

Subsequently, the peripheral nerve cells were detached from the dish using Accutase™ (Innovative Cell Technologies, Inc.). The collected peripheral nerve cells were separated from the medium by centrifugation (1000 rpm, 5 minutes) and were suspended in a DMEM/F12 medium not containing differentiation factors and so on. Centrifugation (1000 rpm, 5 minutes) was performed again to wash the peripheral nerve cells.

The peripheral nerve cells obtained as a precipitate were seeded in two wells of a 6-well plate (diameter of each well: 35 mm, Iwaki & Co., Ltd.) coated with Matrigel™ GFR (the area corresponds to ⅔ times the area of the 60-mm dish, cell seeding density: 6×10$^5$ cells/cm$^2$) under conditions of 5% $CO_2$ and 37° C. for 7 days (culturing in a confluent state).

Test Example (1) Measurement of Expression Levels of Brn3a and Peripherin

Regarding the peripheral nerve cells isolated in Example 1 and Comparative Example 1, the mRNA levels of Brn3a and peripherin, which are conceived to be specifically expressed in peripheral nerve cells, were measured by a real-time RT-PCR method as follows. Total RNA was extracted from the cells to be measured using a NucleoSPin™ RNA II (MACHEREY-NAGEL) RNA extraction kit. Complementary DNA was synthesized using the total RNA as a template with a ReverTra Ace™ qPCR RT Kit (Toyobo Co., Ltd.). The measurement was performed using the synthesized cDNA as a template with a KAPA SYBR™ FAST qPCR kit (Kapa Biosystems, Inc.) and a real time PCR system StepOnePlus™ (Thermo Fisher Scientific Inc.). The target gene expression was quantitatively measured using GAPDH as an endogenous control gene by the delta-delta ct method. Also regarding the peripheral nerve cells isolated in Comparative Example 2, the mRNA level of Brn3a was similarly measured.

(2) Rate of Peripheral Nerve Cells in Culture

Regarding the cultures prepared after completion of the culturing in the step (c) in Example 1 and Comparative Examples 1 and 2, the rates of cells expressing peripheral nerve differentiation markers were measured by FACS using βIII tubulin, peripherin, and Brn3a as indicators as follows. The cells to be measured were detached using Acutase™, and centrifugation was performed for removal of the dissociation solution and washing of the cells. The cell precipitate was suspended in PBS, and the suspension was pressed through a cell strainer (FALCON) to prepare a single cell suspension. The cells were fixed and subjected to cell membrane permeabilization treatment using a FIX & PERM™ Cell Fixation & Cell Permeabilization Kit (Thermo Fisher Scientific Inc.). Subsequently, blocking with PBS containing 5% FBS, 5% goat serum, and 0.1% $NaN_3$ was performed. βIII tubulin was fluorescence-labeled with an Alexa Fluor™ 647 Mouse anti-β-tubulin Class III antibody (BD Biosciences). Peripherin and Brn3a were fluorescence-labeled respectively using an anti-peripherin antibody (Millipore) and an anti-BRN3A antibody (Abcam plc.) each bound to a Zenon™ Rabbit IgG Labeling Kit (Thermo Fisher Scientific Inc.). The cells subjected to only fixation and permeabilization treatment and not fluorescence-labeled were used as a control. The measurement was performed with a FACSVerse™ flow cytometer (BD Biosciences), and data analysis was performed using FlowJo™ software (FLOWJO, LLC).

(3) Morphological Observation

The culture prepared after completion of the culturing in the step (c) of Example 1 was photographed with a microscope in the culture state without being subjected to cell fixation. The microscope used was a PrimoVert camera-integrated microscope (phase difference mode) available from Carl Zeiss.

(4) Results

1) Expression Levels of Brn3a and Peripherin in Example 1 and Comparative Example 1

TABLE 1

| Condition name | Brn3a level | Peripherin level |
|---|---|---|
| Example 1 | 1.00 | 1.00 |
| Comparative Example 1 | 0.063*** | 0.24** |

The Brn3a and Peripherin levels in Comparative Example 1 are shown as relative values with respect to those in Example 1 each defined as 1.00.

: significant at $p<0.01$ (n=3), *: significant at $p<0.001$ (n=3)

2) Expression Levels of Brn3a in Example 1 and Comparative Example 2

TABLE 2

| | Brn3a level | |
|---|---|---|
| Condition name | (1) | (2) |
| Example 1 | 1.00 | 52.52*** |
| Comparative Example 2 | 0.26*** | 13.51*** |

(1) and (2) in Table 2 are the following conditions:

(1) The Brn3a level in Comparative Example 2 is shown as a relative value with respect to that in Example 1 defined as 1.00.

(2) The Brn3a levels in Example 1 and Comparative Example 2 are shown as relative values with respect to that in iPS cells before differentiation defined as 1.00.

***: significant at $p<0.001$ (n=3)

In the peripheral nerve cells manufactured in Example 1, the expression level of Brn3a was 15 times or more higher than that in Comparative Example 1. In addition, the peripherin expression level was 4 times or more compared to that in Comparative Example 1. These results demonstrated that high-purity peripheral nerve cells can be produced by culturing iPS-derived cells differentiated into neural progenitor cells in a confluent state by increasing the seeding density in differentiation into the peripheral nerve cells.

In addition, in the peripheral nerve cells manufactured in Comparative Example 2, the Brn3a expression level was low, about ¼ times, compared to that in Example 1. Furthermore, although the Brn3a expression level in Comparative Example 2 was less than 30 times that of the undifferentiated cells before differentiation, the expression level in Example 1 was 30 times or more.

These results demonstrated that high-purity peripheral nerve cells can be manufactured without decreasing the purity as a result of culturing (differentiation induction) the iPS-derived cells differentiated neural progenitor cells detached once from the dish before differentiation into peripheral nerve cells.

3) Rate of Peripheral Nerve Cells in Culture

TABLE 3

| Condition name | βIII-Tubulin | Peripherin | Brn3a |
|---|---|---|---|
| Example 1 | 97.8% | 96.8% | 90.5% |
| Comparative Example 1 | 79.4% | 57.2% | 47.3% |
| Example 2 | 86.4% | 86.9% | 88.5% |

Figure 2:
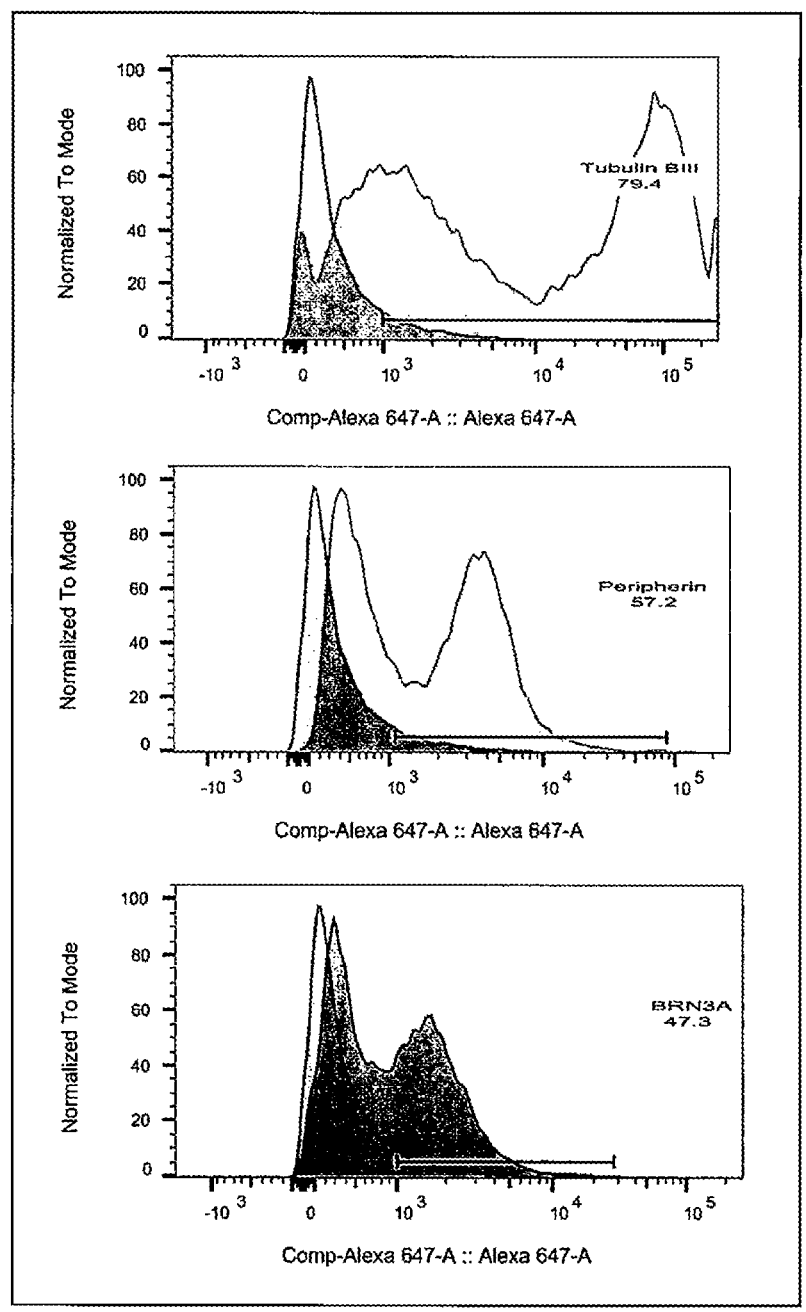

As shown in Table 3 and FIGS. 1 and 2, the rates of βIII tubulin expressing cells, peripherin expressing cells, and Brn3a expressing cells in Examples 1 and 2 were all 85% or more, higher than those in Comparative Example 1. Accordingly, it was further demonstrated that peripheral nerve cells can be efficiently manufactured by performing culturing in a confluent state by increasing the seeding density in differentiation into the peripheral nerve cells.

It was also demonstrated that the peripheral nerve cells were efficiently manufactured at a rate of 85% or more in both cases that the culture period in the step (c) was 21 days (Example 1) and 42 days (Example 2), but the case of 21 days was preferred because of its higher rate.

4) Morphological observation

Figure 3:
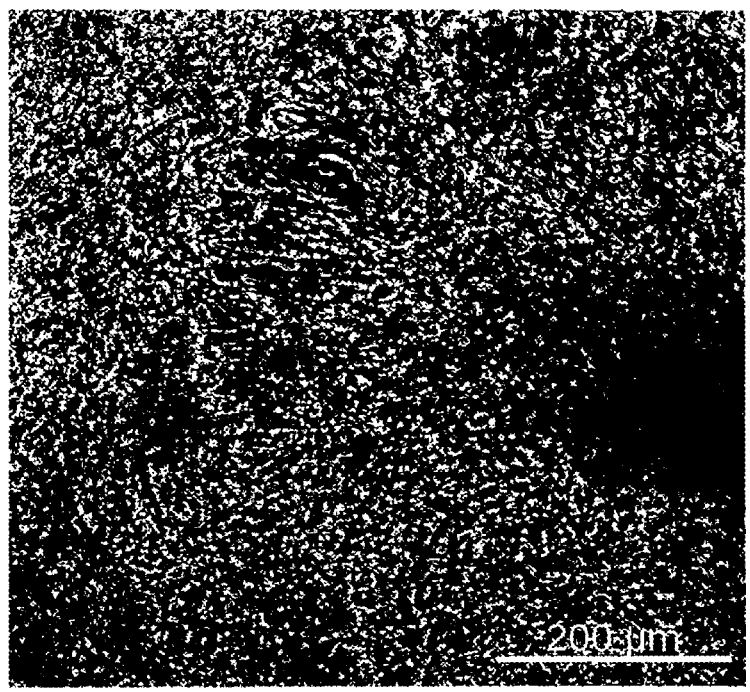
FIG. 3 is a photomicrograph of a culture of peripheral nerve cells (Example 1).

As shown in FIG. 3, in the peripheral nerve cells induced by the method of the present invention, the peripheral nerve cells and axons were densely present, and it was suggested that the purity of the peripheral nerve cells is high.

Comparative Test Example

Peripheral nerve cells were induced from iPS cells by the method shown below in accordance with the method described in Non Patent Literature 1, and the morphology of the resulting peripheral nerve cells was evaluated.

(1) Human iPS Cell

Human iPS cells (iPS cells) used in Example 1 were used.

The iPS cells were seeded in a Matrigel-coated dish and were cultured in ReproFF2 (ReproCELL Inc.) containing penicillin-streptomycin and 10 ng/mL bFGF under conditions of 5% $CO_2$ and 37° C. The medium was replaced by a new one every two days, and subculture was performed when iPS colonies grew.

(2) Differentiation into Neural Progenitor Cells

The iPS cells were detached from the dish using Accutase (Innovative Cell Technologies, Inc.) when the iPS cell colony density reached 50% to 70%. The collected iPS cells were separated from the medium by centrifugation (1000 rpm, 5 minutes). The separated iPS cells were seeded at a cell density of $2\times10^4$ cells/well in a 12-well plate coated with Matrigel™ (Corning Incorporated) and were cultured in a DMEM/F12 medium containing ingredients shown below under conditions of 5% $CO_2$ and 37° C. for 10 days. The medium was replaced by a new one every two or three days.

<Medium Additives>

10% KSR, 1% penicillin-streptomycin, 1% L-glutamine, 0.3 μM SU5402 (Tocris), 1.0 μM RO4929097 (Cellagen Technology), 5 μM CHIR99021 (BioVision Incorporated), 1 μM A83-01 (Cellagen Technology), 0.2 μM LDN-193189 (Cellagen Technology), and 0.1 μM retinoic acid (Sigma-Aldrich).

(3) Differentiation into Peripheral Nerve Cells

The iPS-derived cells differentiated into neural progenitor cells were cultured in a DMEM/F12 medium containing ingredients shown below under conditions of 5% $CO_2$ and 37° C. for 14 days. The medium was replaced by a new one every two or three days.

<Medium Additives>

10% KSR, 1% penicillin-streptomycin, 1% L-glutamine, ×1 N2 supplement, 10 ng/mL NT-3, 10 ng/mL BDNF, 10 ng/mL NGF, 10 ng/mL GDNF, 200 μM ascorbic acid, and 0.5 mM dibutyryl cAMP.

(4) Morphology of Peripheral Nerve Cells

Figure 4:
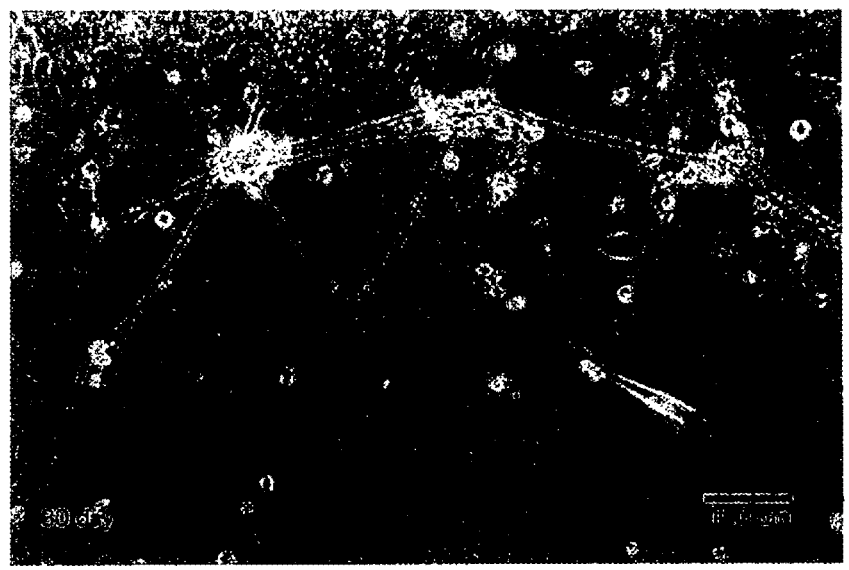
FIG. 4 is a photomicrograph of a culture of peripheral nerve cells (Comparative Test Example).

The culture of the peripheral nerve cells induced by the above-mentioned method was observed under a microscope as in the Test Example (3). However, the microscope used was an Axiovert 100 microscope (phase difference mode, available from Carl Zeiss) connected to a GRCA-R2 camera unit (available from Hamamatsu Photonics K.K.). FIG. 4 shows the results.

FIG. 4 revealed that in the peripheral nerve cells induced by the above-mentioned method, the densities of the peripheral nerve cells and axons were lower than those in the peripheral nerve cells manufactured by the method of Example 1, and the purity of the peripheral nerve cells was low.

(5) Comparison with Literature Values

In Non Patent Literature 1, the Brn3a level expressed in the resulting peripheral nerve cells was about 15 times that defined as 1 in the iPS cells before differentiation. In addition, the rates of the peripheral nerve cells in a culture measured by FACS using βIII tubulin, peripherin, and Brn3a as indicators were reported to be 79.2%, about 78%, and about 15%, respectively. Therefore, the method of the present invention shows significantly high efficiency of differentiation into peripheral nerve cells compared to the method described in Non Patent Literature 1.

The invention claimed is:

1. A method for making peripheral nerve cells, the method comprising:
    (a) culturing mammalian pluripotent cells in a culture vessel in the presence of a culture medium comprising a serum replacement, an FGFR inhibitor, a γ-secretase inhibitor, a GSK3 inhibitor, a TGF-β family inhibitor, an ALK inhibitor, and retinoic acid;
    (b) detaching the cells obtained in (a) after 6 to 14 days; and
    (c) seeding the detached cells at a density of $2\times10^5$ to $6\times10^5$ cells/cm' in a culture vessel; and
    (d) culturing the seeded cells in culture medium comprising a serum replacement, N2 supplement, neurotrophin-3, brain-derived neurotrophic factor, a nerve growth factor, a glial cell line derived growth neurotrophic factor (GDNF), ascorbic acid and dibutyryl cAMP for 21 to 42 days such that peripheral nerve cells expressing βIII tubulin, peripherin, or Brn3a are obtained.

2. The method according to claim 1, wherein (a) further comprises (a'):
    (a') culturing the mammalian pluripotent cells by adherent culture without using feeder cells.

3. The method according to claim 1, wherein the mammalian pluripotent cells are iPS cells.

4. The method according to claim 1, wherein a culture period of the culturing in (d) is 21 to 28 days.

5. The method according to claim 1, wherein the culture medium for the culturing in (d) further comprises an antibiotic.

6. The method according to claim 1, wherein the cells obtained in (a) are detached after the culturing for 8 to 12 days.

7. The method according to claim 1, further comprising:
    (e) recovering the peripheral nerve cells produced in (d).

* * * * *